United States Patent [19]

Hari et al.

[11] Patent Number: 5,380,870
[45] Date of Patent: Jan. 10, 1995

[54] MIXED CRYSTALS OF SULFONATED DIKETOPYRROLOPYRROLES

[75] Inventors: Stefan Hari, Reinach; Olof Wallquist, Marly; Fritz Herren, Düdingen; Thomas Eichenberger, Basel, all of Switzerland

[73] Assignee: Ciba-Geigy Corporation, Ardsley, N.Y.

[21] Appl. No.: 166,750

[22] Filed: Dec. 14, 1993

[30] Foreign Application Priority Data

Dec. 18, 1992 [CH] Switzerland .................. 3894/92

[51] Int. Cl.[6] ........................... C07D 487/04
[52] U.S. Cl. .................... 548/453; 106/493; 106/494; 106/498
[58] Field of Search ........................ 548/453

[56] References Cited

U.S. PATENT DOCUMENTS

| | | | |
|---|---|---|---|
| 4,689,087 | 8/1987 | Spietschka et al. | 548/459 |
| 4,791,204 | 12/1988 | Jost et al. | 548/101 |

FOREIGN PATENT DOCUMENTS

| | | |
|---|---|---|
| 0224445 | 6/1987 | European Pat. Off. |
| 4011927 | 10/1990 | Germany |
| 4037556 | 11/1990 | Germany |
| 2238550 | 11/1990 | United Kingdom |

OTHER PUBLICATIONS

Derwent 90-321772/43 (1990).

*Primary Examiner*—David B. Springer
*Attorney, Agent, or Firm*—Michele A. Kovaleski

[57] ABSTRACT

Mixed crystals of at least two different compounds of formula

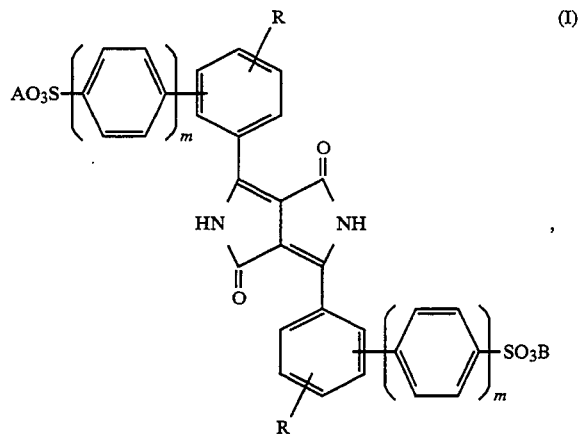

(I)

wherein A and B are each independently of the other a cation of formula

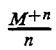

or $N^+H(R_1)(R_2)(R_3)$ M is a mono-, di- or trivalent metal cation, n is 1, 2 or 3, $R_1$, $R_2$ and $R_3$ are each independently of one another hydrogen, $C_1$–$C_{22}$alkyl, $C_7$–$C_{24}$aralkyl, $C_5$–$C_6$cycloalkyl or $C_6$–$C_{18}$aryl, m is 0 or 1, and R is hydrogen, $C_1$–$C_4$alkyl or $C_1$–$C_4$alkoxy, in which compounds of formula I that form the mixed crystals the cations A and B constitute a composite structure

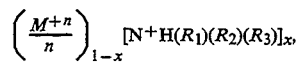

wherein x is a value from 0.2 to 0.8, and the X-ray diffraction pattern of said mixed crystals differs from that of the corresponding compounds in which x is 1 or 0.

These mixed crystals can be used as pigments for colouring organic material of high molecular weight and have exceptional properties, especially dispersibility, heat- and lightfastness.

7 Claims, No Drawings

MIXED CRYSTALS OF SULFONATED DIKETOPYRROLOPYRROLES

The present invention relates to mixed crystals of metal and amine salts of sulfonated 1,4-diketo-3,6-diarylpyrrolopyrroles and to the use thereof for colouring organic material of high molecular weight.

Metal and amine salts of sulfonated 1,4-diketo-3,6-diarylpyrrolopyrroles are disclosed in U.S. Pat. No. 4,791,204 for addition to unsulfonated 1,4-diketopyrrolopyrrole pigments for enhancing certain properties, in particular rheology, heat resistance and deformation. Sulfonated mixtures of at least 3 different 1,4-diketo-3,6-diphenylpyrrolopyrroles can also be used for the same purpose for addition to unsulfonated 1,4-diketopyrrolopyrrole pigments, as disclosed in GB-2 238 550, with in some cases even better results.

Surprisingly, it has now been found that treatment of metal salts of sulfonated 1,4-diketo-3,6-diarylpyrrolopyrroles with amines results in the formation of mixed crystal compounds that are distinguished by unexpectedly superior pigment properties.

Accordingly, the invention relates to mixed crystals of at least two different compounds of formula

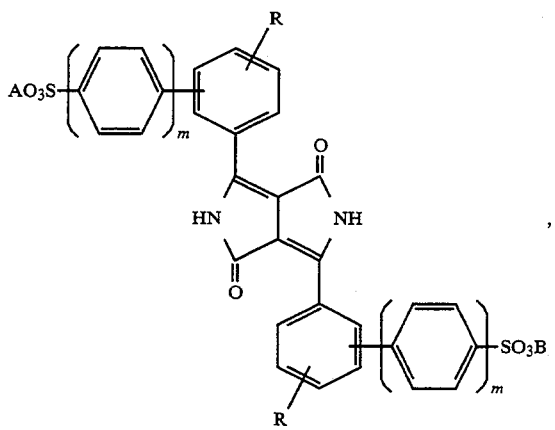

(I)

wherein A and B are each independently of the other a cation of formula

or $N^+H(R_1)(R_2)(R_3)$

M is a mono-, di- or trivalent metal cation, n is 1, 2 or 3, $R_1$, $R_2$ and $R_3$ are each independently of one another hydrogen, $C_1$–$C_{22}$alkyl, $C_7$–$C_{24}$aralkyl, $C_5$–$C_6$cycloalkyl or $C_6$–$C_{18}$aryl, m is 0 or 1, and R is hydrogen, $C_1$–$C_4$alkyl or $C_1$–$C_4$alkoxy, in which compounds of formula I that form the mixed crystals the cations A and B constitute a composite structure

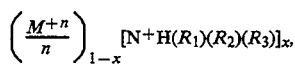

wherein x is a value from 0.2 to 0.8, preferably from 0.35 to 0.65 and, most preferably, from 0.4 to 0.6, and the X-ray diffraction pattern of said mixed crystals differs from that of the corresponding compounds in which x is 1 or 0.

When m is 1, the compounds are compounds of formula

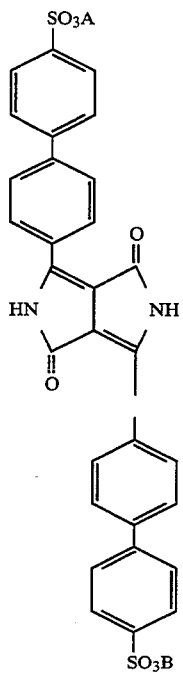

(II)

When A or B is a cation of formula

said cation is typically an alkali metal cation, an alkaline earth metal cation or a transition metal cation, and is preferably $Na^+$, $K^+$, $Mg^{2+}$, $Ca^{2+}$, $Sr^{2+}$, $Ba^{2+}$, $Mn^{2+}$, $Zn^{2+}$, $Cu^{2+}$, $Ni^{2+}$, $Cd^{2+}$, $Fe^{2+}$, $Fe^{3+}$, $Co^{3+}$, $Al^{3+}$ and $Cr^{3+}$. Preferred cations are $Na^+$, $Ca^{2+}$, $Mg^{2+}$, $Sr^{2+}$, $Zn^{2+}$ and $Al^{3+}$.

$R_1$, $R_2$ and $R_3$ defined as $C_1$–$C_{22}$alkyl are typically methyl, ethyl, propyl, isopropyl, n-butyl, sec-butyl, tert-butyl, tert-amyl, octyl, decyl, dodecyl, hexadecyl, stearyl, eicosyl or docosyl.

$R_1$, $R_2$ and $R_3$ defined as $C_7$–$C_{24}$aralkyl are preferably those aralkyl groups that contain a branched or branched alkyl chain containing 1 to 12, preferably 1 to 6 and, most preferably, 1 to 4, carbon atoms (e.g. as described above) and a preferably mono- or bicyclic aryl radical. Typical examples of such groups are benzyl and phenylethyl.

$R_1$, $R_2$ and $R_3$ defined as cycloalkyl are typically cyclopentyl or cyclohexyl.

$R_1$, $R_2$ and $R_3$ defined as $C_6$–$C_{18}$aryl are typically phenyl or naphthyl, preferably unsubstituted phenyl or phenyl which is substituted by halogen such as chloro or bromo, or by $C_1$–$C_4$alkyl or $C_1$–$C_4$alkoxy.

Substituents defined as $C_1$–$C_6$alkoxy are typically methoxy, ethoxy, propoxy, n-butoxy or tert-butoxy.

R defined as $C_1$–$C_4$alkyl is typically methyl, ethyl, propyl, isopropyl, n-butyl or tert-butyl. Methyl and tert-butyl are preferred.

Illustrative examples of $N^+H(R_1)(R_2)(R_3)$ are: $N^+H_4$, $N^+H_3CH_3$, $N^+H_2(CH_3)_2$, $N^+H_3C_2H_5$, $N^+H_2(C_2H_5)_2$, $N^+H_3C_{12}H_{25}$, $N^+H_3C_{18}H_{37}$, $N^+H_3$-cyclohexyl, $N^+H_2(cyclohexyl)_2$, $N^+H_3(CH_3)$ $N^+H_3C_6H_5$, $N^+H_3$-para-toluidine and $N^+H_3$-benzyl.

The mixed crystals as claimed in claim 1 are conveniently prepared by reacting an at least partially water-soluble metal salt of formula

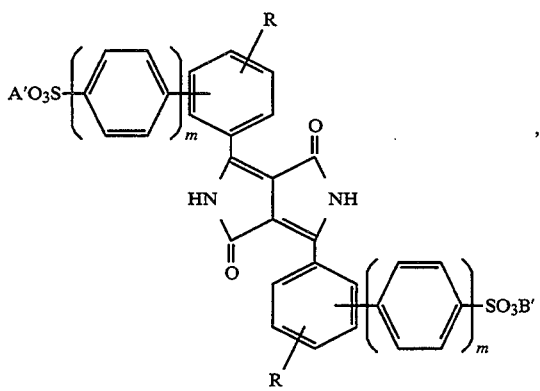 (III)

wherein A' and B' are each independently of the other a cation of formula $$\frac{M^{+n}}{n}$$

as defined above, or preferably both are Na+, with a compound of formula

N+H(R₁)(R₂)(R₃) X'  (IV), wherein X' is an anion that ensures sufficient solubility in water, conveniently a sulfate or, preferably, a chloride, so as to form a composite structure $$\left(\frac{M^{+n}}{n}\right)_{1-x} [N^+H(R_1)(R_2)(R_3)]_x$$

in accordance with the definition given above, in which formulae III and IV above m, R, R₁, R₂ and R₃ have the given meanings, by methods which are known per se.

The reaction is preferably carded out in water, with the optional addition of n-butanol to suppress foaming and to enhance the wettability of the educts, in the temperature range from 60° to 120° C. for 1 to 20 hours.

Instead of adding the ammonium compound of formula IV in the form of the chloride or sulfate it is also possible to add first the equivalent amount of acid (e.g. HCl or H₂SO₄), or a slight excess thereof, and then to add the corresponding free amine of formula N(R₁)(R₂)(R₃). Subsequent Examples 1 and 2 illustrate this last described procedure. The mixed crystals of this invention are preferably obtained by reacting an at least partially water-soluble metal salt of formula III, wherein A and B are Na+, with a mixture of the metal salt of formula

M₁⁺ⁿ (X⁻)ₙ,  (V), wherein M₁ is a metal cation as defined above with the exception of Na, and the ammonium salt of formula

N+H(R₁)(R₂)(R₃) X⁻  (IV), wherein X⁻ is an anion that ensures sufficient solubility in water, preferably Cl⁻.

Instead of the ammonium salt (e.g. in the form of its chloride) it is again possible to add first the equivalent amount of acid, or a slight excess thereof, and then to add a mixture of the metal salt of formula V and the free amine N(R₁)(R₂)(R₃). Subsequent Examples 3 to 6 describe this latter procedure.

The compounds of formulae HI and IV, and hence also V, are known compounds.

Particularly important mixed crystals of this invention are those of at least two different compounds of formula I, wherein A and B are each independently of the other a cation selected from the group consisting of Na+, Ca²+, Ba²+, Mg²+, Sr²+, Zn²+ or Al³+ and N+H(R₁)(R₂)(R₃), wherein R₁, R₂ and R₃ are hydrogen, C₁-C₂₂alkyl or C₅-C₆cycloalkyl, and R, when m=0, is hydrogen, methyl, tert-butyl or methoxy and, when m=1, is hydrogen.

Preferred mixed crystals of this invention are those of at least two different compounds of formula

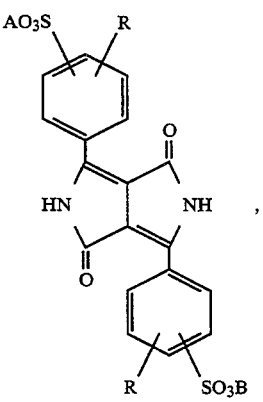 (VI)

wherein R is hydrogen or methyl.

A and B in the above formula VI have the preferred meanings given above.

Also preferred are novel mixed crystals of at least two different compounds of formula II, wherein A and B have the preferred meanings given above.

Especially preferred mixed crystals of this invention are those of at least two different compounds of formula

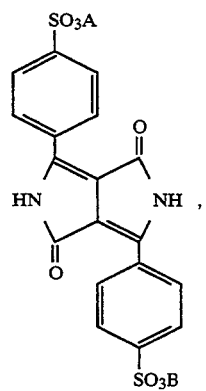 (VII)

wherein A and B have the preferred meanings given above, but are most preferably $$\frac{Sr^{2+}}{2}$$

and $N^+H_3C_8H_{17}$ in the case of the composite structure

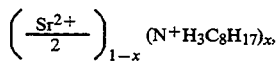

wherein x is a value from 0.4 to 0.6.

Mixed crystals are distinguished by their X-ray diffraction pattern, which differs not only from that of the single components of the mixed crystal but also from that of its physical mixture.

The X-ray diffraction pattern of the mixed crystals of this invention is characterised by lines differing from those that characterise the X-ray diffraction patterns of the corresponding physical mixture and of the corresponding single components.

The mixed crystals of this invention can be used as pigments for colouring organic material of high molecular weight. They can normally be used for this purpose direct in the form in which they are obtained from the synthesis. Depending on the intended end use, the mixed crystals of this invention can be converted into a more opaque or transparent form.

Illustrative examples of organic materials of high molecular weight which can be coloured with the novel mixed crystals are cellulose ethers and esters, typically ethyl cellulose, nitrocellulose, cellulose acetate, cellulose butyrate, natural resins or synthetic resins, typically polymerisation or condensation resins, such as aminoplasts, preferably urea/formaldehyde and melamine/-formaldehyde resins, alkyd resins, phenolic plastics, polycarbonates, polyolefins, polystyrene, polyvinyl chloride, polyamides, polyurethanes, polyesters, ABS polymers, polyphenylene oxides, rubber, casein, silicone and silicone resins, singly or in mixtures.

The mixed crystals of this invention are especially suitable for colouring polyvinyl chloride and polyolefins such as polyethylene and polypropylene as well as ABS polymers.

The above high molecular weight organic compounds may be singly or as mixtures in the form of plastics, melts or of spinning solutions, paints, coating materials or printing inks.

Depending on the end use requirement, it is expedient to use the mixed crystals of this invention as toners or in the form of preparations.

The mixed crystals of this invention can be used in an amount of 0.01 to 30 % by weight, preferably 0.1 to 10 % by weight, based on the high molecular weight organic material.

The pigmenting of the high molecular weight organic materials with the mixed crystals of this invention is conveniently effected by incorporating the pigments by themselves or in the form of masterbatches in the substrates using roll mills, mixing or milling apparatus. The pigmented material is then brought into the desired final form by methods which are known per se, conveniently by calendering, moulding, extruding, coating, spinning, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated before or after working the pigments into the polymers. To obtain different shades it is also possible to add fillers or other chromophoric components such as white, coloured or black pigments in any amount to the high molecular weight organic materials.

For pigmenting paints, coating materials and printing inks, the high molecular weight organic materials and the mixed crystals of this invention, together with optional additives such as fillers, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

When used for colouring e.g. polyvinyl chloride or polyolefins, the mixed crystals of this invention have good allround pigment properties, such as superior colour strength and purity, good fastness to migration and weathering, as well as good hiding power and, most especially, exceptional dispersibility, heat- and lightfastness.

The invention is illustrated by the following Examples.

EXAMPLE 1

157 g of the aqueous paste (c. 31.1%) of the disodium salt of diketopyrrolopyrroledisulfonic acid of formula

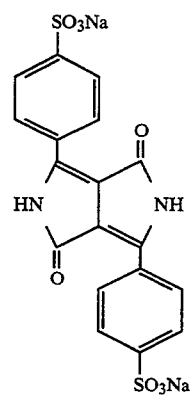

(VIII)

are stirred in 1900 ml of deionised water for 25 minutes at room temperature. To the red suspension are added 100 ml of 1N hydrochloric acid and stirring is continued for 10 minutes. Then 27 g of finely pulverised stearylamine are added and the mixture is heated to 80° C. and becomes a little brighter. The red suspension is stirred for 2 hours at 80° C. and is filtered hot through a filter cloth. The filter product is washed with 4000 ml of deionised water and vacuum dried at 80° C., giving 74 g (100 % of theory) of a red, soft powder for which the following analytical values are obtained:

The calculated values are based on a composite structure $Na^+$: $N^+H_3C_{18}H_{37}$ in the molar ratio of 1:1 (i.e. x=0.5).

| Analysis: | C | H | N | S | Na |
| --- | --- | --- | --- | --- | --- |
| calcd: | 58.44% | 6.81% | 5.68% | 8.67% | 3.11% |
| found: | 58.50% | 7.10% | 5.70% | 8.24% | 2.36% |

The X-ray diffraction pattern was measured on an X-ray diffractometer D500, supplied by Siemens, with Cu-K-alpha-radiation. The d values of the strongest lines (d>3.0 Å) are recorded in the following Table together with the visually estimated relative line intensities.

| d-value in Å | Intensity |
| --- | --- |
| 19.2 | average |
| 12.8 | weak |
| 9.6 | strong |
| 8.5 | weak |
| 7.9 | weak |
| 7.3 | average |
| 6.4 | weak |
| 5.2 | weak |
| 5.0 | very strong |
| 4.6 | weak |
| 4.3 | average |
| 4.1 | weak |
| 4.0 | weak |
| 3.7 | average |
| 3.6 | average |
| 3.4 | very strong |
| 3.2 | weak |
| 3.1 | weak |
| 3.0 | weak |

EXAMPLE 2

Example 1 is repeated, with the sole exception that 11 ml of cyclohexylamine are used instead of stearylamine under identical conditions, giving 53 g (90 % of theory) of a red powder containing 1 equivalent of water of crystallisation. The following analytical values are obtained for this product:

| Analysis: | C | H | N | S | Na |
| --- | --- | --- | --- | --- | --- |
| calcd: | 49.06% | 4.46% | 7.15% | 10.91% | 3.91% |
| found: | 49.00% | 4.27% | 7.07% | 10.95% | 4.62% |

The calculated values are based on a composite structure $Na^+:N^+H_3C_6H_{11}$ in the molar ratio 1:1.

EXAMPLES 3–6 a is suspended at room temperature in a mixture of 3000 ml of water and 150 ml of n-butanol and the suspension is heated to 90° C. After 1 hour b is added and the mixture is again stirred at 90° C. for 1 hour. Then a mixture of c and d is added and the somewhat viscous, but still readily stirrable, red suspension is kept for another 18 hours at 90° C. The product is filtered through a hard paper filter and the filtrate is washed with 2000 ml of water and vacuum dried at 120° C.

In Examples 3–6, a, b, c and d each denote the following:

EXAMPLE 3 a: 122 g of the compound of formula VIII (Example 1), 93%
b: 253 ml of 1 N HCl
c: 34 g of $SrCl_2.6H_2O$
d: 39 ml of n-octylamine Yield: 137 g (93% of theory) of a dark red powder containing 1.25 equivalents of water of crystallisation. The following analytical values are obtained for this product:

| Analysis: | C | H | N | S | Sr |
| --- | --- | --- | --- | --- | --- |
| calcd: | 48.57% | 5.09% | 6.53% | 9.97% | 6.81% |
| found: | 48.38% | 4.64% | 6.41% | 10.20% | 7.69% |

½ $Sr^{2+}$: $N^+H_3C_8H_{19}$ = 1:1.

EXAMPLE 4 a: 122 g of the compound of formula VIII (Example 1), 93%.
b: 253 ml of 1 N HCl.
c: 25 g of $CaCl_2.6H_2O$.
d: 63 g of stearylamine, finely powdered.

Yield: 166 g (96% of theory) of a red powder containing 1 equivalent of water of crystallisation. The following analytical values are obtained for this product:

| Analysis: | C | H | N | S | Ca |
| --- | --- | --- | --- | --- | --- |
| calcd: | 57.27% | 6.94% | 5.56% | 8.49% | 2.65% |
| found: | 57.20% | 6.70% | 5.80% | 8.70% | 2.56% |

½$Ca^{2+}$:$N^+H_3C_{18}H_{37}$ = 1:1.

EXAMPLE 5 a: 122 g of the compound of formula VIII (Example 1), 93%.
b: 253 ml of 1 N HCl
c: 28 g of $MgCl_2.6H_2O$
d: 39 g of n-octylamine Yield: 122 g (88 % of theory) of a red powder containing 1 equivalent of water of crystallisation. The following analytical values are obtained for this product:

| Analysis: | C | H | N | S | Mg |
| --- | --- | --- | --- | --- | --- |
| calcd: | 51.46% | 5.32% | 6.92% | 10.57% | 2.00% |
| found: | 51.50% | 5.40% | 6.96% | 10.24% | 1.58% |

½ $Mg^{2+}$:$N^+H_3C_8H_{19}$=1:1.

Example 6 a: 121 g of the compound of formula

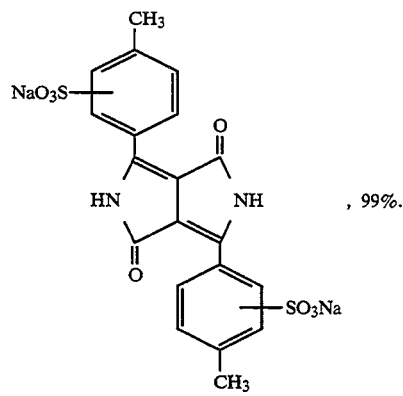
, 99%.

b: 266 ml of 1 N HCl.
c: 31 g of $SrCl_2.6H_2O$.
d: 68 g of stearylamine, finely powdered.

Yield: 196 g (97% of theory) of a dark red powder for which the following analytical values are obtained:

| Analysis: | C | H | N | S | Sr |
| --- | --- | --- | --- | --- | --- |
| calcd: | 57.86% | 6.90% | 5.33% | 8.13% | 5.55% |
| found: | 57.98% | 7.72% | 5.22% | 7.24% | 4.00% |

½ $Sr^{2+}$:$N^+H_3C_{18}H_{37}$=1:1.

All the products obtained in Examples 1-6 can be termed mixed crystals, as their X-ray diffraction patterns always differ significantly from those of the corresponding mixtures of the single components, i.e. the pure metal and alkylammonium salts.

All the products mentioned in Examples 1-6 exhibit very good fastness to migration, heat and light in polyvinyl chloride, polyolefins and ABS polymers.

What is claimed is:

1. Mixed crystals of at least two different compounds of formula

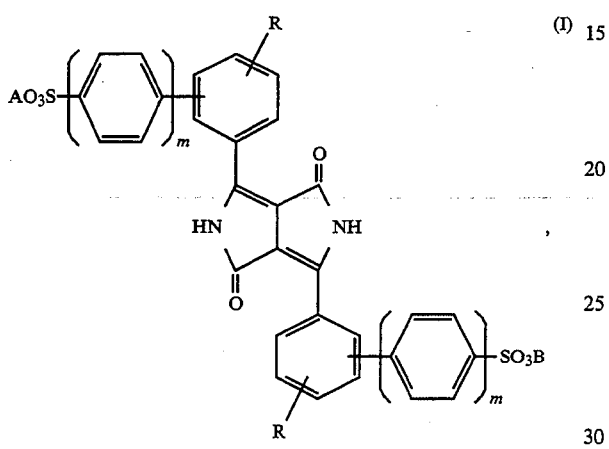

(I)

wherein A and B are each independently of the other a cation of formula

or $N^+H(R_1)(R_2)(R_3)$ M is an alkali metal cation, an alkaline earth metal cation or a transition metal cation, n is 1, 2 or 3, $R_1$, $R_2$ and $R_3$ are each independently of one another hydrogen, $C_1$-$C_{22}$alkyl, $C_7$-$C_{24}$aralkyl, $C_5$-$C_6$-cycloalkyl or $C_6$-$C_{18}$aryl, m is 0 or 1, and R is hydrogen, $C_1$-$C_4$alkyl or $C_1$-$C_4$alkoxy, in which compounds of formula I that form the mixed crystals the cartions A and B constitute a composite structure

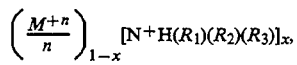

wherein x is a value from 0.2 to 0.8 and the X-ray diffraction pattern of said mixed crystals differs from that of the corresponding compounds in which x is 1 or 0.

2. Mixed crystals according to claim 1, wherein x is a numerical value from 0.35 to 0.65.

3. Mixed crystals according to claim 2 of at least two different compounds of formula I, wherein A and B are each independently of the other a cation selected from the group consisting of $Na^+$, $Ca^{2+}$, $Ba^{2+}$, $Mg^{2+}$, $Sr^{2+}$, $Zn^{2+}$ or $Al^{3+}$ or $N^+H(R_1)(R_2)(R_3)$, wherein $R_1$, $R_2$ and $R_3$ are hydrogen, $C_1$-$C_{22}$alkyl or $C_5$-$C_6$cycloalkyl, and R, when m=0, is hydrogen, methyl, tert-butyl or methoxy and, when m=1, is hydrogen.

4. Mixed crystals according to claim 3 of at least two different compounds of formula

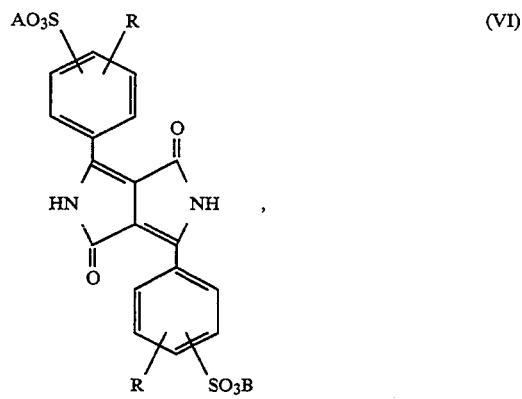

(VI)

wherein R is hydrogen or methyl.

5. Mixed crystals according to claim 3 of at least two different compounds of formula

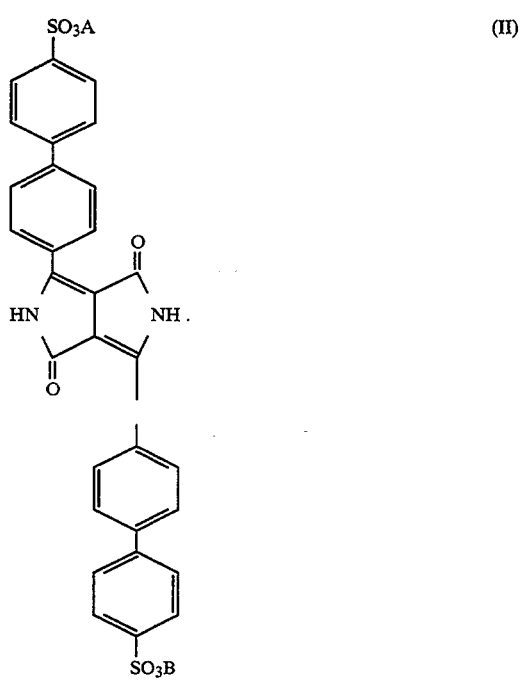

(II)

6. Mixed crystals according to claim 4 of at least two different compounds of formula

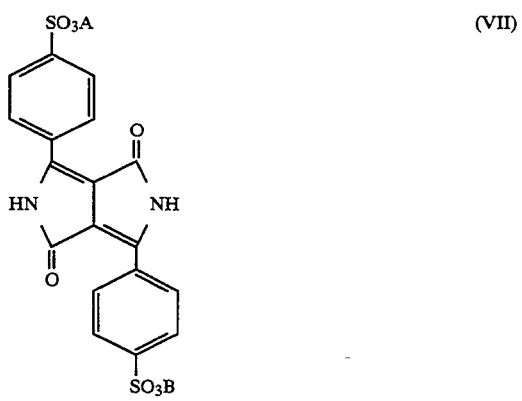

(VII)

7. Mixed crystals according to claim 6, wherein A and B are each independently of the other $$\frac{Sr^{2+}}{2}$$

and $N^+H_3C_8H_{17}$ in which compounds of formula (VII) that form the mixed crystals the cations A and B constitute a composite structure $$\left(\frac{Sr^{2+}}{2}\right)_{1-x}(N^+H_3C_8H_{17})_x,$$

wherein x is a numerical value from 0.4 to 0.6.

* * * * *